United States Patent [19]
Maier

[11] Patent Number: 6,121,187
[45] Date of Patent: Sep. 19, 2000

[54] AMORPHOUS, MICROPOROUS MIXED OXIDE CATALYSTS WITH CONTROLLED SURFACE POLARITY FOR SELECTIVE HETEROGENEOUS CATALYSIS, ADSORPTION AND MATERIAL SEPARATION

[75] Inventor: Wilhelm F. Maier, Mülheim an der Ruhr, Germany

[73] Assignee: Studiengesellschaft Kohle mbH, Mulheim an der Ruhr, Germany

[21] Appl. No.: 09/077,478

[22] PCT Filed: Nov. 22, 1996

[86] PCT No.: PCT/EP96/05162

§ 371 Date: Oct. 26, 1998

§ 102(e) Date: Oct. 26, 1998

[87] PCT Pub. No.: WO97/20630

PCT Pub. Date: Jun. 12, 1997

[30] Foreign Application Priority Data

Dec. 2, 1995 [DE] Germany .............. 195 45 042

[51] Int. Cl.[7] .............. B01J 21/08; B01J 21/06; B01J 21/12; B01J 21/14
[52] U.S. Cl. .............. 502/232; 502/233; 502/234; 502/235; 502/236; 502/237; 502/238; 502/239; 502/240; 502/241; 502/242; 502/243; 502/244; 502/245; 502/246; 502/247; 502/248; 502/249; 502/250; 502/251; 502/252; 502/253; 502/254; 502/255; 502/256; 502/257; 502/258; 502/259; 502/260; 502/261; 502/262; 502/263

[58] Field of Search ............. 502/232, 233, 502/234, 235, 236, 237, 238, 239, 240, 241, 242, 243, 244, 245, 246–263

[56] References Cited

FOREIGN PATENT DOCUMENTS

| | | |
|---|---|---|
| 2 148 637 | 4/1972 | Germany . |
| 2 165 027 | 7/1972 | Germany . |
| 2 229 015 | 12/1972 | Germany . |
| 2 311 822 | 9/1973 | Germany . |
| 4 419 195 | 1/1995 | Germany . |

*Primary Examiner*—Elizabeth D. Wood
*Attorney, Agent, or Firm*—Norris, McLaughlin & Marcus, P.A.

[57] ABSTRACT

The present invention relates to amorphous microporous mixed oxides, characterized by having, in dried form, a narrow pore size distribution (half width <±10% of the pore diameter) of micropores with diameters in the range of <3 nm and a total surface area of between 20 and 1000 m²/g, containing a fraction of from 0.1 to 20% by weight of non-hydrolyzable organic groups, and to a process for the preparation of such oxides.

6 Claims, 3 Drawing Sheets

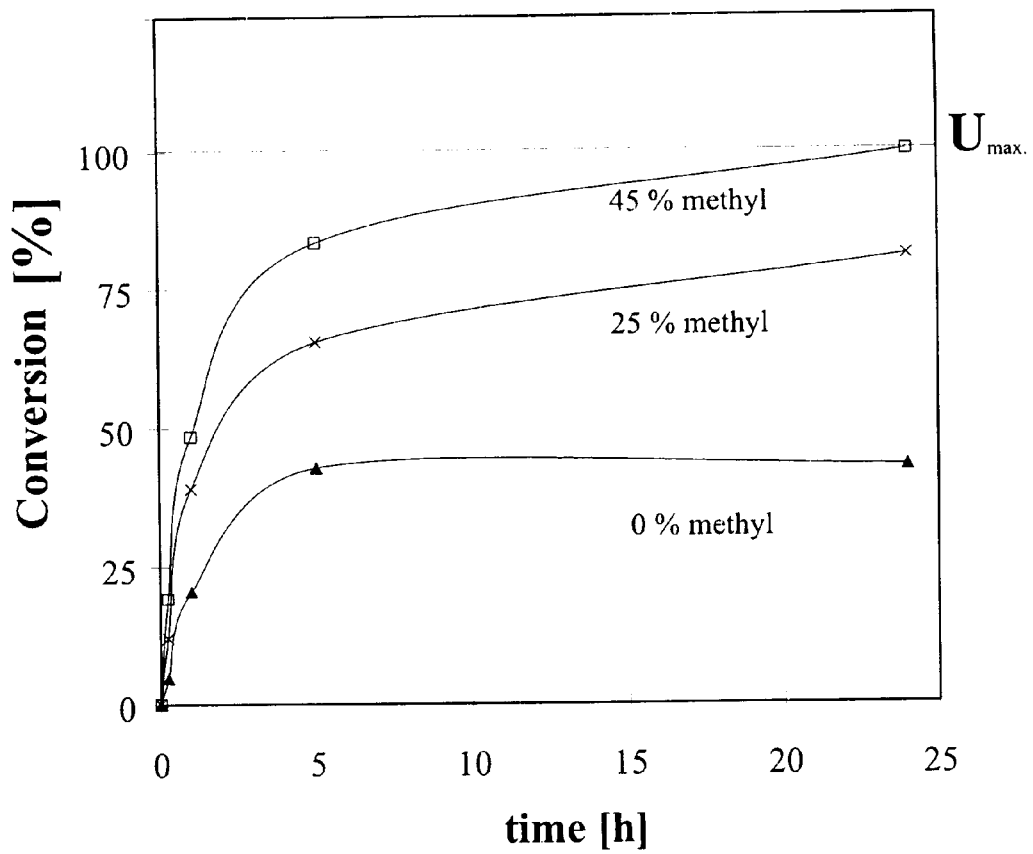
Figure 1: Dependence of the yield of the epoxidation of 1-octene with TBHP on the content of methyl-containing Si-groups, X, of amorphous, microporous titanium dioxide/silicon dioxide/methyl-silicon sesquioxide glasses (1 $TiO_2$ : 99-x $SiO_2$ : x $MeSiO_{1.5}$).

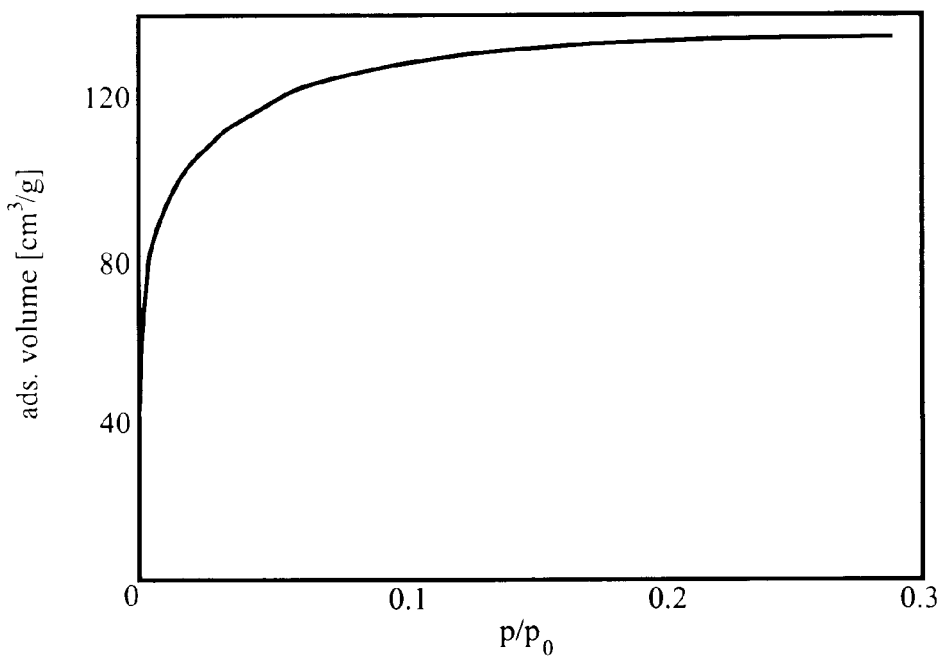
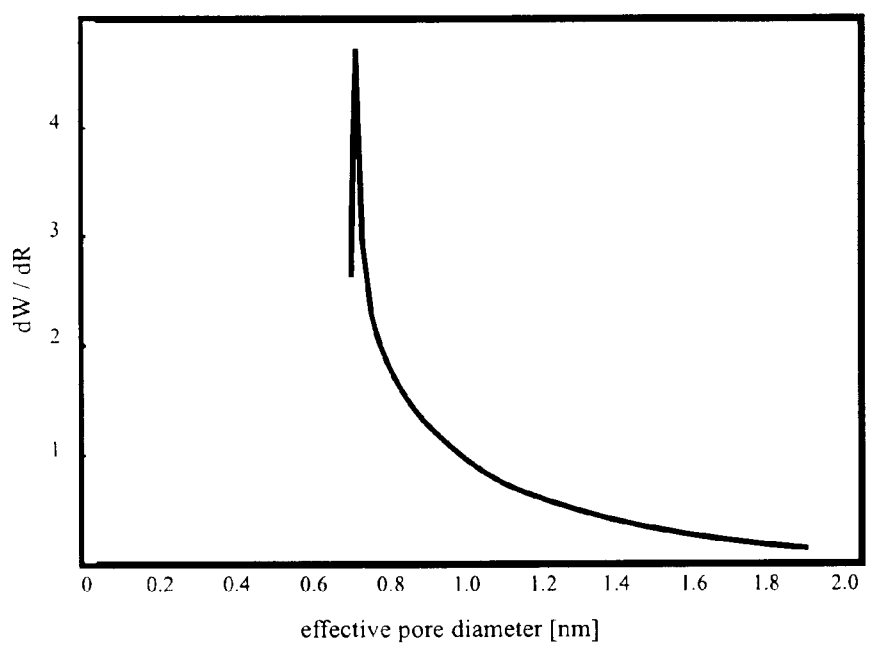
Figure 2: Typical adsorption isotherm and micropore size distribution of an amorphous aluminium oxide/silicon oxide /methyl silicon sesquioxide glass (Ti:Si:MeSi = 1:79:20)

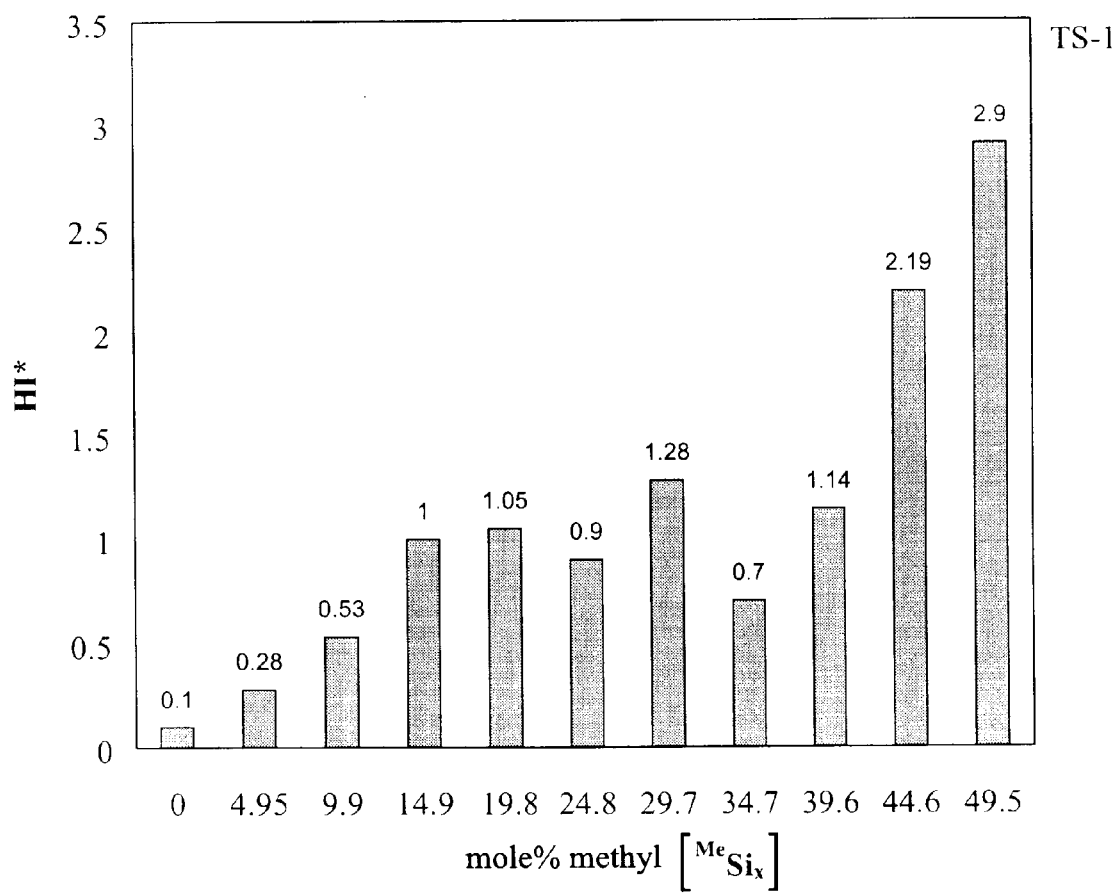
Figure 3: Dependence of the hydrophobicity index HI on the content of methyl groups of amorphous, microporous titanium dioxide/silicon dioxide/methylsilicon sesquioxide glasses (1 $TiO_2$ : 99-x $SiO_2$ : x $MeSiO_{1.5}$). The HI of TS-1, measured under identical conditions, is entered at the top as a reference line.

AMORPHOUS, MICROPOROUS MIXED OXIDE CATALYSTS WITH CONTROLLED SURFACE POLARITY FOR SELECTIVE HETEROGENEOUS CATALYSIS, ADSORPTION AND MATERIAL SEPARATION

This application is a 371 of PCT/EP96/05162 filed on Nov. 22, 1996.

BACKGROUND OF THE INVENTION

1. Field of the Invention

The present invention relates to novel highly porous catalyst materials in which the polarity of the interior surfaces can be purposefully adjusted. Said materials consist of mixed oxides which contain from 0.1 to 20% by weight of chemically bound organic residues. These organic residues serve to purposefully control the hydrophobicity of the materials and thus to improve the conversion, residence time and selectivity of heterogeneously catalyzed reactions.

2. Description of Related Art

An as yet unsolved problem concerns the polarity of the interior surfaces of heterogeneous catalysts which is hardly controllable. This surface polarity affects the interaction of the catalyst with the reactants, products and the solvent or other accompanying substances. With a good catalyst, this interaction is balanced in such a way that reactants and products will rapidly and effectively diffuse within the pore system of the catalyst whereas accompanying substances and side products are essentially kept out of the catalyst. Zeolites normally absorb water so well that they are widely used as desiccants. Therefore, before being used as catalysts, they must be dried most thoroughly at temperatures of up to 500° C. There are exceptions, however. Thus, it is known that zeolites with a silicalite structure sorb very little water despite of their high interior surface area, which indicates a certain hydrophobicity (E. M. Flanigen, I. M. Bennett, R. W. Grose, J. P. Cohen, R. L. Polton, R. Kirchener, J. V. Smith, Nature 272 (1978), 437). This hydrophobicity is considered responsible for the special properties of Ti-containing silicalites (TS-1, TS-2) as selective catalysts (T. Tatsumi, K. Asano, K. Yanagisawa in Studies in Surface Science and Catalysis 84 (1994), 1861). While hydrophilic catalysts, such as microporous mixed-oxide glasses or Y zeolites, are not suitable for oxidation with $H_2O_2$, the crystalline Ti silicalites, which are suitable for oxidation with $H_2O_2$, are not capable of utilizing tert-butyl hydroperoxide (TBHP) as an oxidant.

The water absorbtivity of ZSM zeolites linearly depends on their Al content (D. H. Olsen, W. O. Haag, R. M. Lago, J. Catal. 61 (1980) 390). This hydrophobicity is the reason for the activity of Ti-containing silicalites (TS-1, TS-2) as selective oxidation catalysts with hydrogen peroxide as the oxidant. In contrast, the comparatively hydrophilic amorphous $TiO_2/SiO_2$ materials of the same composition cannot utilize $H_2O_2$ as an oxidant (Sheldon, J. Mol. Catal. 7 (1980), 107). With these materials, t-butyl hydroperoxide can be used as an oxidant for selective oxidations; however, these catalysts tend to be rapidly deactivated (R. A. Sheldon, J. A. Van Doorn, J. Catal. 31 (1973), 427). To date, silicalites have been the only heterogeneous catalysts which can use $H_2O_2$ as an oxidant for selective oxidations under mild conditions. However, their hydrophobicity decreases as the Ti content increases, so that a contrary effect occurs as the fraction of catalytically active sites increases (Tatsumi et al., Stud. Surf. Sci. Catal. 84 (1994), 1861).

The particular importance of surface polarity also becomes evident in the use of zeolites in adsorption technology. Dealumination can produce hydrophobic zeolites which can be employed for adsorptive waste air cleaning and solvent recovery (Otten et al., Chem. Ing. Tech. 64 (1992), 915). The water absorption of other zeolites, however, cannot be suppressed as completely as that of the silicalites (Gunzel et al., Chem. Ing. Tech. 61 (1989), 66).

To conclude, very few zeolite structures can be rendered hydrophobic by dealumination, and thus, an extremely limited selection of materials are available for heterogeneous catalysis and adsorption in the presence of water under mild conditions. Moreover, dealumination is a comparatively cumbersome additional process step which mostly leads to a significant loss of structure, the formation of defect sites and a significant increase of undesirable amorphous fractions in the zeolite. In addition, the extent of dealumination cannot be purposefully adjusted, and the effect of a dealumination performed on the desired process must be established empirically. A known method for changing the surface polarity is subsequent modification. Thus, accessible surface hydroxy groups of catalysts can be subsequently modified by silylation with known silylating agents, such as $(CH_3)_3SiCl$ or $((CH_3)_3Si)_2NH$ (DE 23 11 822 C2), or other reagents. This subsequent modification has several drawbacks. The silylation in pores alters the pore geometry and thus possibly shape selectivities; hydroxy groups in micropores of <1 nm can not or but incompletely be modified because of the bulky reagents; and the hydroxy groups thus silylated or alkylated are bound to the surface only through an O bridge to form a $(CH_3)_3Si$—O— linkage or R—O— linkage, and thus remain prone to hydrolysis. Therefore, there is a great need for novel highly porous materials in which the polarity of the surface can be purposefully adjusted in the preparation thereof independently of their elemental composition.

SUMMARY OF THE INVENTION

We have now found that the polarity of the interior and exterior surfaces of highly porous oxides, and mixed oxides can be adjusted by copolycondensating alkyloxy- or aryloxysilanes containing non-hydrolyzable R' groups of the type R'—$Si(OR)_3$ with the other components of the sol-gel process for the preparation of the porous oxides. Thus, catalysts with controlled hydrophobicity can be prepared in one process step. The preparation and composition of these materials can be stated briefly as follows:

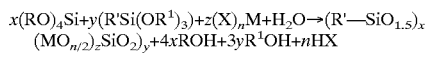

where R and $R^1$ are suitable alkyl or aryl groups which may be the same or different, R' is the non-hydrolyzable organic group which changes the hydrophilicity of the material, and M is an element of the group consisting of Si, Ti, Al, Mo, Sn, Zn, V, Mn, Fe, Co, Ni, As, Pb, Sb, Bi, Ru, Re, Cr, W, Nb, Hf, La, Ce, Gd, Ga, In, Tl, Ag, Cu, Li, K, Na, Be, Mg, Ca, Sr and Ba and mostly represents the carrier of the catalytic activity. The X's are the ligands of the soluble metal compounds, preferably halides, alkoxides, oxyalkoxides, carboxylates, oxalates, nitrates, sulfates, sulfonates, sulfides, acetylacetonates, glycolates or aminoalkoxylates. The base material in this example is $SiO_2$ which may be replaced by $Al_2O_3$, $TiO_2$ or $ZrO_2$, resulting in the following hydrophobic glasses:

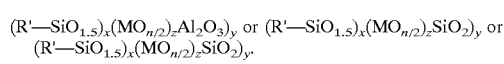

The process herein presented is an especially optimized polycondensation process which is directed to obtain a true chemical mixture of the alkoxides and salts employed, essentially free of domains and with a high porosity and narrow pore size distribution. Our process works under mild conditions without the use of templates or other additives. It can dispense with the use of technically cumbersome hydrothermal conditions, high pressure and supercritical reaction conditions and is basically different from other preparation processes for mixed oxides. Subsequent modification of the catalysts as a second process step is avoided, and the $CH_3Si$— group anchored in the matrix through three oxygen linkages is a component of the solid matrix with high thermal and long-term stabilities. A special additional feature of the materials according to the invention is the generation of the narrow pore size distribution with pores of <3 nm which promises a special fine tuning of the shape-selective and redox-selective properties of the catalyst in compounds with the controllable surface polarity.

BRIEF DESCRIPTION OF THE DRAWINGS

The invention will now be described in more detail with reference to the drawings, wherein:

FIG. 1 is a graph depicting the dependence of the yield of the epoxidation of 1-octene with TBHP on the content of methyl-containing Si-groups, X, of amorphous, microporous titanium dioxide/silicon dioxide/methyl-silicon sesquioxide glasses (1 $TiO_2$: 99-x $SiO_2$: x $MeSiO_{1.5}$).

FIG. 2 is a combination of two graphs depicting the typical adsorption isotherm and micropore size distribution of an amorphous aluminum oxide/silicon oxide/methyl silicon sesquioxide glass (Ti:Si:MeSi=1:79:20).

FIG. 3 is a graph depicting the dependence of the hydrophobicity index HI on the content of methyl groups of amorphous, micrcoporous titanium dioxide/silicon dioxide/methyl silicon sesquioxide glasses (1 $TiO_2$ : 99-x $Sio_2$: x $MeSiO_{1.5}$). The HI of TS-1, measured under identical conditions, is entered at the top as a reference line.

According to the invention, highly porous amorphous Ti-containing silicon dioxides are prepared which catalyze the selective epoxidation of olefins with hydrogen peroxide comparably well or better than the known zeolites TS-1 and TS-2. Thus, under standardized conditions, 11% of cyclohexene oxide is obtained from cyclohexene with $H_2O_2$ using a glass containing methyl groups (1% Ti, 25% Me—Si, 74% Si) while only <2% of epoxide is obtained with TS-1. We have found that propene with TBHP gives twice the yield of propylene oxide (selectivity >97%) with a hydrophobic Ti glass (3% Ti, 45% Me—Si, 55% Si) as compared with a glass free of methyl groups under the same reaction conditions. In contrast, TS-1 yields no conversion with TBHP. While propylene in methanol with hydrogen peroxide preferably yields propylene oxide when a hydrophobic TiSi glass is used, no propylene oxide can be detected with a TiSi glass free of methyl groups under comparable conditions.

DETAILED DESCRIPTION OF THE INVENTION

The influence on the acid-catalyzed formation of t-butyl ether from isobutene with n-hexanol and 1-naphthol was examined in a competitive reaction. The formation of dimers and oligomers of isobutene as side-products was to be suppressed, and selectivity for one of the two alcohols was to be achieved. While the formation of almost 25% of isobutene dimers, based on the ethers formed, occurs in methyl-free Sn-containing Si glass (3% Sn, 97% Si), no dimer formation can be detected in the product with methyl-containing Sn—Si glass (30% Me—Si, 3% Sn, 67% Si). With methyl-free Al-containing Si glass (3% Al, 97% Si), the formation of isobutene dimers predominates, and the yield is around 67% naphthol t-butyl ether and 37% n-hexyl t-butyl ether. With methyl-containing Al-Si glass (10% Me—Si, 3% Al, 87% Si), only 30% isobutene dimers form, relatively to the ether formation, and the yield of ethers increases to 57% n-hexyl t-butyl ether and 43% naphthol t-butyl ether. This suppression of dimer formation and change of the ether selectivity with increasing methyl content of the glasses is continued in Zr-containing glasses.

The reactions stated in the following were performed under comparable conditions at low conversions. The ammoxidation of cyclohexanone with $H_2O_2$ and ammonia gives a six times higher yield of oxime (27%) with Ti—Si glasses containing methyl groups as compared to Ti—Si glasses free of methyl groups (5%). From toluene and $H_2O_2$, the benzyl hydroperoxide forms in high selectivity with the glass containing methyl groups (1% Ti, 25% Me—Si, 74% Si) while no hydroperoxide forms with TS-1, and the yield is decreased to $\frac{1}{10}$ with the methyl-free glass.

The activity-preserving effect of the covalent incorporation of organic groups in amorphous porous glasses on the catalytic activity under standardized conditions can be seen in FIG. 1 from the epoxidation of 1-octene with TBHP. If 45% of all Si atoms in the glass have covalently bound methyl groups, the conversion increases from a maximum of 40% in the methyl-free glass to 100% in the methyl-containing glass. The early deactivation of the methyl-free glasses is observed in many reactions and is due to an obstruction of the pores, presumably by product molecules, since these deactivated catalysts can apparently be completely regenerated as often as desired by baking out.

Such amorphous hydrophobic glasses can be prepared by the solgel process described herein in one synthetic step from tetraethoxysilane, methyltriethoxysilane and isopropoxytitanium. It is of particular importance to this invention that the elemental components of the finished catalyst are homogeneously mixed rather than being present in domains. Thus, they are true chemical mixed oxides. In the preparation of the sol, in which all components of the final product are already contained, it is important that a true solution exists during the gelling and no phase separation occurs. Thus, the materials described herein are all based on a preparation process in which at least 1–50 mole % of R'—$Si(OR)_3$ is added to the sol-gel mixture. Suitable non-hydrolyzable R' groups are basically any chemical groups which can form a covalent non-hydrolyzable stable bond to silicon. However, simple groups, such as methyl, ethyl, isopropyl, —$C_nH_{2n+1}$ and phenyl, are preferably employed. It is also possible, however, to use the full functionality of Organic Chemistry by employing functionalized groups as R', such as —$C_nH_{2n}Cl$, —$C_nH_{2n}NH_2$, —$C_nH_{2n}COOH$, —$C_nH_{2n}OH$, —$C_nH_{2n}CF_3$, —$CH_2$—$CH$=$CH_2$, —$CH_2COCH_3$, —$CH_2NR_4^+$ or o-, m- or p-functionalized aryl groups. These functionalized groups enable exact adjustment of the diffusion and adsorption of reactants by specific interactions with particular substrate molecules. Further, controlled slow drying of the gels is of particular importance in order to obtain a uniform, known narrow pore size distribution. FIG. 2 shows the adsorption isotherm and the micropore distribution (according to Horvath-Kawazoe) of an Al—Si glass containing methyl groups.

The mixed oxides thus obtained are distinct from all other shape-selective or highly porous mixed oxide catalysts in that the catalyst contains a defined fraction of non-hydrolyzable organic residues covalently bound to silicon atoms. These residues are prominently responsible for the catalytic activity and selectivity of the catalyst. They are distinct from the known materials (Enichem, EP OS 0 492 697 A1) in that the catalysts now described are materials having the described narrow pore size distribution and a homogeneous element distribution, and that our materials contain more than 1 mole % of non-hydrolyzable organic components.

The material herein presented does not necessarily have micropores. Larger-pore hydrophobic catalyst materials can also be prepared by this process.

The characterization of the surface polarity of the thus prepared glasses can be effected by different methods. Since our materials can be prepared to be highly porous with pores ranging to the purely microporous range of the crystalline zeolites, we have employed for the characterization a method developed for zeolite characterization (Berke, Kiss, Kleinschmit, Weitkamp, Chem. Ing. Tech. 63 (1991), 623). Thus, an inert gas saturated with water vapor and n-octane was passed at 30° C. over a fixed bed of the freshly dried amorphous mixed oxide (standardized grain fraction and quantity), and the breakthrough time of the components in gas chromatography was determined. As a quantitative measure of the hydrophobicity, the hydrophobicity index HI can be used which is calculated from the ratio of the final loads of the material. FIG. 3 shows the dependence of the hydrophobicity index of amorphous microporous silicon oxides with 1 titanium oxide on the varying content of non-hydrolyzable methyl groups. The HI measured in our laboratory for the extremely hydrophobic TS-1 serves as a reference standard.

With the materials herein described, the surface polarity of the exterior and interior surfaces of oxides and mixed oxides can be controlled in such a way that the diffusion of different molecules into the materials is hindered or promoted depending on their polarities alone. The process is applicable not only to microporous materials, but also to mesoporous materials, such as, e.g., the MCM catalysts, if they are produced from alkoxysilanes as described in Mobil Oil, U.S. Pat. No. 5,134,242, P. T. Tanev, M. Chibwe, T. J. Pinnavia, Nature 368 (1994), 321). The materials herein presented can be employed for the selective catalysis of isomerization reactions, hydrogenation reactions, oxidation reactions with atmospheric oxygen, hydrogen peroxide or organic peroxides and peracids, alkylation and acylation reactions, disproportionation reactions, hydrogenation and dehydrogenation reactions, hydration and dehydration reactions, condensation reactions, coupling reactions, substitution reactions, cycloaddition and cycloreversion reactions, redox reactions, ether formation, esterification and transesterification reactions, crude-oil cracking and hydrocracking. They are suitable for selective catalysis as well as for the separation of gases and liquids. They may be used as ion-exchangers or as adsorbents. They are also suitable for the formation of ultrafiltration membranes and gas separation membranes, and for the formation of catalysts with selective cavities for molecular recognition (DE-A-43 09 660). Membranes made of these materials are suitable, e.g., for the separation of alcohol and water as well as for the removal of carbon dioxide from air, of methane from mine gas or town gas, the purification of stale air with retention of water and carbon dioxide, the separation of carbon monoxide and hydrogen, oxygen-nitrogen separation, the selective removal of hydrogen from gas mixtures, the recovery of organic solvents, and the selective separation of polar or non-polar components from air, exhaust air, flue gases, kitchen air and polluted air from air-conditioning plants.

EXAMPLE 1

Amorphous, microporous titanium dioxide/silicon dioxide/methylsilicon sesquioxide glass (1 $TiO_2$: 79.2 $SiO_2$: 19.8 $MeSiO_{1.5}$)

8 ml of tetraethoxysilane (TEOS), 1.8 ml of methyltriethoxysilane (MTES), 0.133 ml of tetraisopropoxytitanium (TIPOT) and 7.9 ml of ethanol are successively dissolved in one another, and 1.98 ml of 8 N HCl is added with stirring. The gel, after hardening, is heated to 65° C. under a protective gas at a heating rate of 0.2° C./min, kept at this temperature for 3 h, brought to 250° C. at a heating rate of 0.2° C./min, and calcined at this temperature for another 3 h. Adsorption/desorption isotherms show that the material has a monomodal distribution of the micropore sizes; $S_{BET}$= 545 m$^2$/g, pore diameter: 0.72 nm.

EXAMPLE 2

Amorphous, microporous titanium dioxide/silicon dioxide/methylsilicon sesquioxide glasses of composition 1 $TiO_2$: 50.95–100 $SiO_2$: 0–49.5 $MeSiO_{1.5}$ By analogy with Example 1, titanium dioxide/silicon dioxide/methylsilicon sesquioxide glasses were prepared from 10 ml of TEOS (BET: 585 m$^2$/g, pore diameter: 0.73 nm), 9.5 ml of TEOS and 0.45 ml of MTES (BET: 489 m$^2$/g, pore diameter: 0.74 nm), 9 ml of TEOS and 0.9 ml of MTES (BET: 627 m$^2$/g, pore diameter: 0.73 nm), 8.5 ml of TEOS and 1.35 ml of MTES (BET: 527 m$^2$/g, pore diameter: 0.73 nm), 8.0 ml of TEOS and 1.8 ml of MTES (BET: 545 m$^2$/g, pore diameter: 0.72 nm), 7.5 ml of TEOS and 2.23 ml of MTES (BET: 532 m$^2$/g, pore diameter: 0.73 nm), 7.0 ml of TEOS and 2.76 ml of MTES (BET: 639 m$^2$/g, pore diameter: 0.74 nm), 6.5 ml of TEOS and 3.15 ml of MTES (BET: 575 m$^2$/g, pore diameter: 0.73 nm), 6.0 ml of TEOS and 3.6 ml of MTES (BET: 625 m$^2$/g, pore diameter: 0.73 nm), 5.5 ml of TEOS and 4.05 ml of MTES (BET: 574 m$^2$/g, pore diameter: 0.72 nm), and 5 ml of TEOS and 4.5 ml of MTES (BET: 580 m$^2$/g, pore diameter: 0.73 nm), while the same procedure was employed as in Example 1 and the same amounts of TIPOT (0.133 ml), ethanol (7.9 ml) and 8 N HCl (1.98 ml) were used.

EXAMPLE 3

Amorphous, microporous titanium dioxide/silicon dioxide/phenylsilicon sesquioxide glass By analogy with Example 1, a gel of composition 1 $TiO_2$: 64.35 $SiO_2$: 34.65 $(C_6H_5)SiO_{1.5}$ was obtained from 6.5 ml of TEOS, 3.78 ml of phenyltriethoxysilane, 0.133 ml of TIPOT and 7.9 ml of ethanol by adding 1.98 ml of 8 N HCl, which gel was subjected to the calcination process described in Example 1.

EXAMPLE 4

Amorphous, microporous titanium dioxide/silicon dioxide/ethylsilicon sesquioxide glass By analogy with Example 1, a gel of composition 1 $TiO_2$: 89 $SiO_2$: 10 $(C_2H_5)SiO_{1.5}$ was obtained from 9 ml of TEOS, 0.96 ml of ethyltriethoxysilane, 0.133 ml of TIPOT and 7.9 ml of ethanol by adding 1.98 ml of 8 N HCl, which gel was subjected to the calcination process described in Example 1.

EXAMPLE 5

Amorphous, microporous titanium dioxide/silicon dioxide/n-propylsilicon sesquioxide glass By analogy with Example 1, a gel of composition 1 $TiO_2$: 89 $SiO_2$: 10 $(C_3H_7)SiO_{1.5}$ was obtained from 9 ml of TEOS, 0.79 ml of n-propyltrimethoxysilane, 0.133 ml of TIPOT and 7.9 ml of ethanol by adding 1.98 ml of 8 N HCl, which gel was subjected to the calcination process described in Example 1.

EXAMPLE 6

Amorphous, microporous titanium dioxide/silicon dioxide/isobutylsilicon sesquioxide glass By analogy with Example 1, a gel of composition 1 $TiO_2$: 89 $SiC_2$: 10 $(C_4H_9)SiC_{1.5}$ was obtained from 9 ml of TEOS, 1.12 ml of isobutyltriethoxysilane, 0.133 ml of TIPOT and 7.9 ml of ethanol by adding 1.98 ml of 8 N HCl, which gel was subjected to the calcination process described in Example 1.

EXAMPLE 7

Amorphous, microporous titanium dioxide/silicon dioxide/n-hexylsilicon sesquioxide glass By analogy with Example 1, a gel of composition 1 $TiO_2$: 64.35 $SiO_2$: 34.65 $(n-C_6H_{13})SiO_{1.5}$ was obtained from 6.5 ml of TEOS, 3.60 ml of n-hexyltrimethoxysilane, 0.133 ml of TIPOT and 7.9 ml of ethanol by adding 1.98 ml of 8 N HCl, which gel was subjected to the calcination process described in Example 1.

EXAMPLE 8

Amorphous, microporous aluminum oxide/silicon dioxide/methylsilicon sesquioxide glasses By analogy with Example 1, aluminum oxide/silicon dioxide/methylsilicon sesquioxide glasses of composition 1.5 $Al_2O_3$: 97 $SiO_2$: 0 $MeSiO_{1.5}$ (0.176 ml of tris(sec-butoxy)aluminum, 5 ml of TEOS), 1.5 $Al_2O_3$: 92.15 $SiO_2$: 4.85 $MeSiO_{1.5}$ (0.176 ml of tris(sec-butoxy)aluminum, 4.75 ml of TEOS, 0.22 ml of MTES) and 1.5 $Al_2O_3$: 87.3 $SiO_2$: 9.7 $MeSiO_{1.5}$ (0.176 ml of tris(sec-butoxy)aluminum, 4.5 ml of TEOS, 0.44 ml of MTES) were prepared using 4.2 ml of ethanol and 1 ml of 8 N HCl in each case. The procedure of gel preparation and calcination can be seen from Example 1.

EXAMPLE 9

Amorphous, microporous zirconium oxide/silicon dioxide/methylsilicon sesquioxide glasses By analogy with Example 1, zirconium oxide/silicon dioxide/methylsilicon sesquioxide glasses of composition 3 $ZrO_2$: 97 $SiO_2$: 0 $MeSiO_{1.5}$ (0.311 ml of tetra-n-propoxyzirconium (70% in n-propanol), 5 ml of TEOS), 3 $ZrO_2$: 92.15 $SiO_2$: 4.85 $MeSiO_{1.5}$ (0.311 ml of tetra-n-propoxyzirconium (70% in n-propanol), 4.75 ml of TEOS, 0.22 ml of MTES) and 3 $ZrO_2$: 87.3 $SiO_2$: 9.7 $MeSiO_{1.5}$ (0.311 ml of tetra-n-propoxyzirconium (70% in n-propanol), 4.5 ml of TEOS, 0.44 ml of MTES) were prepared using 4.2 ml of ethanol and 1 ml of 8 N HCl in each case. The procedure of gel preparation and calcination can be seen from Example 1.

EXAMPLE 10

Amorphous, microporous tin oxide/silicon dioxide/methylsilicon sesquioxide glasses By analogy with Example 1, tin oxide/silicon dioxide/methylsilicon sesquioxide glasses of composition 3 $SnO_2$: 97 $SiO_2$: 0 $MeSiO_{1.5}$ (0.435 ml of tin(II) ethylhexanoate, 10 ml of TEOS), 3 $SnO_2$: 87.3 $SiO_2$: 9.7 $MeSiO_{1.5}$ (0.435 ml of tin(II) ethylhexanoate, 9 ml of TEOS, 0.9 ml of MTES), 3 $SnO_2$: 77.6 $SiO_2$: 19.4 $MeSiO_{1.5}$ (0.435 ml of tin(II) ethylhexanoate, 8 ml of TEOS, 1.8 ml of MTES) and 3 $SnO_2$: 67.9 $SiO_2$: 29.1 $MeSiO_{1.5}$ (0.435 ml of tin(II) ethylhexanoate, 7 ml of TEOS, 2.7 ml of MTES) were prepared using 4.2 ml of ethanol and 1 ml of 8 N HCl in each case. The procedure of gel preparation and calcination can be seen from Example 1.

EXAMPLE 11

Amorphous, microporous vanadium oxide/silicon dioxide/methylsilicon sesquioxide glasses By analogy with Example 1, vanadium oxide/silicon dioxide/methylsilicon sesquioxide glasses of composition 2.5 $V_2O_5$: 95 $SiO_2$: 0 $MeSiO_{1.5}$ (0.66 g of vanadylacetylacetonate, 11 ml of TEOS), 2.5 $V_2O_5$: 85.5 $SiO_2$: 9.5 $MeSio_{1.5}$ (0.66 g of vanadylacetylacetonate, 10 ml of TEOS, 1 ml of MTES), 2.5 $V_2O_5$: 76 $SiO_2$: 19 $MeSiO_{1.5}$ (0.66 g of vanadylacetylacetonate, 9 ml of TEOS, 2 ml of MTES) and 2.5 $V_2O_5$: 66.5 $SiO_2$: 28.5 $MeSiO_{1.5}$ (0.66 g of vanadylacetylacetonate, 7.8 ml of TEOS, 3 ml of MTES) were prepared using 9 ml of ethanol and 2.25 ml of 8 N HCl in each case. The procedure of gel preparation and calcination can be seen from Example 1.

EXAMPLE 12

Amorphous, microporous manganese oxide/silicon dioxide/methylsilicon sesquioxide glasses By analogy with Example 1, manganese oxide/silicon dioxide/methylsilicon sesquioxide glasses of composition 3% Mn, 97% Si: 0% MeSi (1.344 mmol of Mn(II) acetate, 44.8 mmol of TEOS), 3% Mn, 87% Si: 10% MeSi (1.34 mmol of Mn(III) acetate, 40.3 mmol of TEOS, 4.5 mmol of MTES), 3% Mn, 77% Si: 20% MeSi (1.34 mmol of Mn(III) acetate, 35.9 mmol of TEOS, 9 mmol of MTES), 3% Mn, 67% Si: 30% MeSi (1.34 mmol of Mn(III) acetate, 31.4 mmol of TEOS, 13.5 mmol of MTES), 3% Mn, 57% Si: 406 MeSi (1.34 mmol of Mn(III) acetate, 26.9 mmol of TEOS, 17.9 mmol of MTES) and 3% Mn, 48.5% Si: 48.5% MeSi (1.34 mmol of Mn(III) acetate, 22.4 mmol of TEOS, 22.4 mmol of MTES) were prepared using 8.1 ml of ethanol and 2 ml of 8 N HCl in each case. The components were charged in a 50 ml PP beaker in the following order: TEOS, MTES, Mn(III) acetate·2$H_2O$ and ethanol. The hydrochlorid acid was added dropwise with stirring. After 5 min of stirring, the beaker was loosely covered until gelling was complete. The procedure of gel preparation and calcination can be seen from Example 1.

EXAMPLE 13

Amorphous, microporous chromium oxide/silicon dioxide/methylsilicon sesquioxide glasses By analogy with Example 1, chromium oxide/silicon dioxide/methylsilicon sesquioxide glasses of composition 3% Cr, 97% Si: 0% MeSi (1.344 mmol of Cr(O—iPr)$_3$, 44.8 mmol of TEOS), BET: 468 $m^2$/g; 3% Cr, 87% Si: 10% MeSi (1.34 mmol of Cr(O—iPr)$_3$, 40.3 mmol of TEOS, 4.5 mmol of MTES), 571 $m^2$/g; 3% Cr, 77% Si: 20% MeSi (1.34 mmol of Cr(O—iPr)$_3$, 35.9 mmol of TEOS, 9 mmol of MTES), 3% Cr, 67% Si: 30% MeSi (1.34 mmol of Cr(O—iPr)$_{31}$, 31.4 mmol of TEOS, 13.5 mmol of MTES), 3% Cr, 57% Si: 40%

MeSi (1.34 mmol of Cr(O—iPr)$_3$, 26.9 mmol of TEOS, 17.9 mmol of MTES) and 3% Cr, 48.5% Si: 48.5% MeSi (1.34 mmol of Cr(O—iPr)$_3$, 22.4 mmol of TEOS, 22.4 mmol of MTES) were prepared using 8.1 ml of ethanol and 2 ml of 8 N HCl in each case. The components were charged in a 50 ml PP beaker in the following order: TEOS, MTES, Cr(O—iPr)$_3$ and ethanol. The hydrochlorid acid was added dropwise with stirring. After 5 min of stirring, the beaker was loosely covered until gelling was complete. The procedure of gel preparation and calcination can be seen from Example 1.

EXAMPLE 14

Amorphous, microporous iron oxide/silicon dioxide/methylsilicon sesquioxide glasses By analogy with Example 1, iron oxide/silicon dioxide/methylsilicon sesquioxide glasses of composition 3% Fe, 97% Si: 0% MeSi (1.344 mmol of Fe(O—iPr)$_3$, 44.8 mmol of TEOS); 3% Fe, 87% Si: 10% MeSi (1.34 mmol of Fe(O—iPr)$_3$, 40.3 mmol of TEOS, 4.5 mmol of MTES); 3% Fe, 77% Si: 20% MeSi (1.34 mmol of Fe(O—iPr)$_3$, 35.9 mmol of TEOS, 9 mmol of MTES), 3% Fe, 67% Si: 30% MeSi (1.34 mmol of Fe(O—iPr)$_3$, 31.4 mmol of TEOS, 13.5 mmol of MTES), 3% Fe, 57% Si: 40% MeSi (1.34 mmol of Fe(O—iPr)$_3$, 26.9 mmol of TEOS, 17.9 mmol of MTES) and 3% Fe, 48.5% Si: 48.5% MeSi (1.34 mmol of Fe(O—iPr)$_3$, 22.4 mmol of TEOS, 22.4 mmol of MTES) were prepared using 8.1 ml of ethanol and 2 ml of 8 N HCl in each case. The components were charged in a 50 ml PP beaker in the following order: TEOS, MTES, Fe(O—iPr)$_3$ and ethanol. The hydrochlorid acid was added dropwise with stirring. After 5 min of stirring, the beaker was loosely covered until gelling was complete. The procedure of gel preparation and calcination can be seen from Example 1.

EXAMPLE 15

Amorphous, microporous antimony oxide/zirconium dioxide/titanium dioxide/methylsilicon sesquioxide glass 10.00 ml of Ti(O—iPr)$_4$, 1.54 ml of Zr(O—nBu)$_4$, 0.63 g of Sb(OBu)$_3$, 3.88 mmole (0.7 g)of MeSi(OEt)$_3$ and 10.65 ml of n-1-butanol are successively dissolved in one another under Ar. The clear solution is stirred for 15 min. After the addition of 10.65 ml of absolute n-1-butanol, stirring was continued for another 15 min. Then, hydrolysis was performed by adding dropwise 1.09 ml of 12.5 N HCl. Stirring of the solution was continued under Ar for 3 h, and then the solution was loosely covered and allowed to stand in air until gelling was complete.

EXAMPLE 16

Amorphous, microporous tin dioxide/zirconium dioxide/methylsilicon sesquioxide glass To 10.25 ml of Zr(O—n—C$_3$H$_7$)$_4$ (70% solution in propanol) and 3.35 mmole (0.6 g) of MeSi(OEt)$_3$ under argon was added a solution consisting of 6.25 ml of isopropanol abs., 0.20 ml of HNO$_3$ (14 M) and 1.87 ml of acetylacetone. The solution was stirred for 15 min. This was followed by the addition of 0.646 g of Sn(2-ethylhexanoate)$_2$. After stirring for another 15 min, hydrolysis was performed. For this purpose, a solution of 6.25 ml of isopropanol abs., 0.30 ml of HNO$_3$ (14 M) and 1.88 ml of H$_2$O was added dropwise. The clear solution was stirred under Ar for 5 h and then loosely covered and allowed to stand in air until gelling was complete.

EXAMPLE 17

Amorphous, microporous chromium oxide/aluminum oxide/methylsilicon sesquioxide glass 10.00 g of Al(O—sBu)$_3$, 4.26 mmole (0.76 g) of MeSi(OEt)$_3$ and 0.458 g of Cr(O—iPr)$_3$ were mixed under Ar. After stirring for 15 min, 8.16 ml of isopropanol was added. Then, complexation was effected by adding dropwise 4.40 ml of acetylacetone. This was accompanied by a strong evolution of heat. The solution turned yellowish. After the addition of acid (3.04 ml HNO$_3$ (14 M)) and stirring for 15 min, hydrolysis was performed with a solution of 8.16 ml of isopropanol and 1.53 ml of water. The clear brownish solution was stirred under Ar for 2 h and then loosely covered and allowed to stand in air until gelling was complete.

EXAMPLE 18

Epoxidation of 1-octene with tert-butyl hydroperoxide (TBHP)

15.0 mmol of 1-octene, 1 ml of TBHP solution (3 M in isooctane) and 50 mg of titanium dioxide/silicon dioxide/methylsilicon sesquioxide glass (1 TiO$_2$: 54.45 SiO$_2$: 44.55 MeSiO$_{1.5}$) were stirred at 80° C. for 24 h, and the composition of the product was determined by gas chromatography. The conversion was complete, and the epoxide selectivity was 96%.

EXAMPLE 19

Epoxidation of 1-octene with tert-butyl hydroperoxide (TBHP)

15.0 mmol of 1-octene, 1 ml of TBHP solution (3 M in isooctane) and 50 mg of vanadium oxide/silicon dioxide/methylsilicon sesquioxide glass (2.5 V$_2$O$_5$: 66.5 SiO$_2$: 28.5 MeSiO$_{1.5}$) were stirred at 80° C. for 20 h, and the composition of the product was determined by gas chromatography. The conversion was 68%, and an epoxide selectivity of 74% was achieved.

EXAMPLE 20

Monoepoxidation of trans,trans,trans-1,5,9-cyclododecatriene (all-trans CDT) with tert-butyl hydroperoxide (TBHP)

15.0 mmol of all-trans CDT, 1 ml of TBHP solution (3 M in isooctane), 2 ml of isooctane and 50 mg of titanium dioxide/silicon dioxide/methylsilicon sesquioxide glass (1 TiO$_2$: 48.5 SiO$_2$: 48.5 MeSiO$_{1.5}$) were stirred at 80° C. for 24 h, and the composition of the product was determined by gas chromatography. The conversion was 88%, and the monoepoxide selectivity was 89.3%.

EXAMPLE 21

Epoxidation of propene with tert-butyl hydroperoxide (TBHP)

150 mg of microporous amorphous Ti—Si oxide catalyst (4.8% Ti) was charged in a 200 ml steel autoclave and suspended in 10 ml of TBHP solution (3 M in isooctane). Then, the autoclave was sealed and pressurized with 3.2 g of propene. The reaction was performed with stirring (magnetic stirring bar) at a temperature of 60° C. for a period of 3 h; thereafter, the reactor was cooled, the catalyst was removed by centrifugation, and the composition of the clear reaction solution was analyzed by gas chromatography. The following composition of the product was found: 0.4% propene, 5.0% propylene oxide.

EXAMPLE 22

Oxidation of propene with a hydrophobic Ti—Si glass 75 mg of catalyst (titanium dioxide/silicon dioxide/methylsilicon sesquioxide glass (1 $TiO_2$: 49.5 $SiO_2$: 49.5 $MeSiO_{1.5}$)) was charged in a 100 ml steel autoclave and suspended in 5 ml of TBHP solution (3 M in isooctane). Then, the autoclave was sealed and pressurized with 1.6 g of propene. The reaction was performed with stirring (magnetic stirring bar) at a temperature of 60° C. for a period of 3 h; thereafter, the reactor was cooled, the catalyst was removed by centrifugation, and the composition of the clear reaction solution was examined by gas chromatography. The following composition of the product was found: 0.8% propene, 10.3% propylene oxide. The yield was twice of that obtained with the hydrophilic Ti—Si glass.

EXAMPLE 23

Selective oxidation of ethanol to acetaldehyde with aqueous hydrogen peroxide solution 21 mmol of ethanol, 7 mmol of $H_2O_2$ (25% in water) and 50 mg of titanium dioxide/silicon dioxide/methylsilicon sesquioxide glass (1 $TiO_2$: 54.45 $SiO_2$: 44.55 $MeSiO_{1.5}$) were stirred at 45° C. for 18 h, and the composition of the product was determined by gas chromatography. An ethanol conversion of 14.8% was achieved with an acetaldehyde selectivity of 91.8%.

EXAMPLE 24

Epoxidation of cyclohexene with aqueous hydrogen peroxide solution 2 mmol of cyclohexene, 4 mmol of $H_2O_2$ (25% in water) and 20 mg of titanium dioxide/silicon dioxide/methylsilicon sesquioxide glass (1 $TiO_2$: 67.9 $SiO_2$: 29.1 $MeSiO_{1.5}$) were stirred at 50° C. for 15 h, and the composition of the product was determined by gas chromatography. A cyclohexene conversion of 24.0% and an epoxide selectivity of 57.8% were found.

EXAMPLE 25

Epoxidation of all-trans cyclododecatriene with aqueous hydrogen peroxide solution 2 mmol of all-trans cyclododecatriene, 4 mmol of $H_2O_2$ (25% in water) and 20 mg of titanium dioxide/silicon dioxide/methylsilicon sesquioxide glass (1 $TiO_2$: 64.3 $SiO_2$: 34.7 $MeSiO_{1.5}$) were stirred at 50° C. for 15 h, and the composition of the product was determined by gas chromatography. A cyclohexene conversion of 24.0% and an epoxide selectivity of 57.8% were found.

EXAMPLE 26

Ammoxidation of cyclohexanone to cyclohexanone oxime with aqueous hydrogen peroxide solution and aqueous ammonia solution 5 mmol of cyclohexanone, 7.5 mmol of ammonia (25% in water) and 50 mg of titanium dioxide/silicon dioxide/methylsilicon sesquioxide glass (1 $TiO_2$: 54.45 $SiO_2$: 44.55 $MeSiO_{1.5}$) were stirred at 60° C., and 5 mmol of $H_2O_2$ (25% in water) was added at this temperature within 4 h. After another 2 h at 60° C., a cyclohexanone conversion of 31% has taken place (from gas chromatography). A cyclohexanone oxime selectivity of 9.1% was calculated.

EXAMPLE 27

Selective oxidation of toluene with aqueous hydrogen peroxide solution 13 mmol of toluene, 4.5 mmol of $H_2O_2$ (25% in water), 3.1 ml of acetonitrile and 25 mg of titanium dioxide/silicon dioxide/methylsilicon sesquioxide glass (1 $TiO_2$: 54.45 $SiO_2$: 44.55 $MeSiO_{1.5}$) were stirred at 80° C. for 18 h, and the composition of the product was determined by gas chromatography. A toluene conversion of 4.3% was achieved with a product selectivity (benzaldehyde+benzyl hydroperoxide) of 90.5%.

EXAMPLE 28

Selective oxidation of ethylbenzene with aqueous hydrogen peroxide solution 13 mmol of ethylbenzene, 4.5 mmol of $H_2O_2$ (25% in water), 3.1 ml of acetonitrile and 25 mg of titanium dioxide/silicon dioxide/methylsilicon sesquioxide glass (1 $TiO_2$: 60 $SiO_2$: 39 $MeSiO_{1.5}$) were stirred at 80° C. for 18 h, and the composition of the product was determined by gas chromatography. An ethylbenzene conversion of 6.8% was achieved with a product selectivity for acetophenone of 57% and for 2-phenylethanol of 14.9%.

EXAMPLE 29

Hydroxylation of benzene to phenol with aqueous hydrogen peroxide solution 3.36 mmol of benzene, 6.6 mmol of $H_2O_2$ (25% in water), 5 ml of acetone and 35 mg of vanadium oxide/silicon dioxide/methylsilicon sesquioxide glass (2.5 $V_2O_5$: 76 $SiO_2$: 19 $MeSiO_{1.5}$) were stirred at 60° C. for 4 h, and the composition of the product was determined by gas chromatography. A benzene conversion of 2.6% was achieved with a phenol selectivity of 91%.

EXAMPLE 30

Etherification to form tert-butyl ethers

In a 200 ml autoclave, 300 mmol of isobutene, 50 mmol of 1-hexanol, 50 mmol of 1-naphthol and 300 mg of tin oxide/silicon dioxide/methylsilicon sesquioxide glass of composition 3 $SnO_2$: 97 $SiO_2$: 0 $MeSiO_{1.5}$ were stirred at a pressure of 40 bar $N_2$ and at a temperature of 140° C. for 16 h. Analysis of the product mixture by gas chromatography gave a yield of 1-naphthyl tert-butyl ether of 39.5% (based on 1-naphthol) as compared to a yield of 1-hexyl tert-butyl ether of 63.6% (based on 1-hexanol). In an analogous way, when the catalyst 1.5 $Al_2O_3$: 97 $SiO_2$: 0 $MeSiO_{1.5}$ was used, a yield of 1-naphthyl tert-butyl ether of 67.6% and a yield of 1-hexyl tert-butyl ether of 37.4% were achieved.

When the catalyst 3 $ZrO_2$: 97 $SiO_2$: 0 $MeSiO_{1.5}$ was used, a yield of 1-naphthyl tert-butyl ether of 24.4% and a yield of 1-hexyl tert-butyl ether of 46.1% were achieved.

In addition, larger fractions of isobutene dimers and trimers were formed.

EXAMPLE 31

Etherification to form tert-butyl ethers

By analogy with the procedure described in Example 20, a tin oxide/silicon dioxide/methylsilicon sesquioxide of composition 3 $SnO_2$: 67.9 $SiO_2$: 29.1 $MeSiO_{1.5}$ gave yields of 1-naphthyl tert-butyl ether and 1-hexyl tert-butyl ether of 4.6% and 17.2%, respectively. In an analogous way, when the catalyst 1.5 $Al_2O_3$: 87.3 $SiO_2$: 9.7 $MeSiO_{1.5}$ was used, a yield of 1-naphthyl tert-butyl ether of 43.5% and a yield of 1-hexyl tert-butyl ether of 56.6% were achieved.

When the catalyst 3 $ZrO_2$: 87.3 $SiO_2$: 9.7 $MeSiO_{1.5}$ was used, a yield of 1-naphthyl tert-butyl ether of 28.4% and a yield of 1-hexyl tert-butyl ether of 33.4% were achieved.

The reactions proceeded without the formation of isobutene oligomers.

EXAMPLE 32

Alkylation of aromatics 75 mg of aluminum oxide/silicon oxide/methylsilicon sesquioxide (3 $Al_2O_3$: 10 $MeSiO_{1.5}$: 87 $SiO_2$), diluted with the same amount of quartz sand, was baked out in a stream tube at 350° C. in a stream of oxygen. A liquid mixture of toluene/ethanol (1:3) is continuously metered at 1 ml/h into the $N_2$ inert gas stream (flow rate 4 ml/min) and passed together over the catalyst bed at 300° C. The product gas stream shows a quantitative conversion to ethyltoluenes.

EXAMPLE 33

Formation of propylene oxide with hydrogen peroxide 1.9 ml of 25% $H_2O_2$, 1.6 ml of propene (l), 75 mg of titanium dioxide/silicon dioxide/methylsilicon sesquioxide (1 $TiO_2$: 45 $MeSiO_{1.5}$: 54 $SiO_2$) and 3.1 ml of methanol was heated at 60° C. in a sealed autoclave for 3 h. Apart from propene oxide, nothing could be detected in the product. In a parallel experiment with Al—Si glass free of methyl groups under comparable conditions, no PO could be detected.

What is claimed is:

1. Amorphous microporous mixed oxides having, in dried form, a narrow pore size distribution (half width <±10% of the pore diameter) of micropores with diameters in the range of <3 nm, a homogeneous element distribution, a total surface area between 20 and 1000 $m^2/g$, and a fraction of from 0.1 to 20% by weight of non-hydrolyzable organic groups.

2. The amorphous microporous mixed oxides according to claim 1, wherein at least 50% of said mixed oxides consists of one or a mixture of oxides of titanium, silicon, aluminum or zirconium.

3. The amorphous microporous mixed oxides according to claim 1, wherein at least 50% of said mixed oxide consists of one or a mixture of oxides of titanium, silicon, aluminum or zirconium, and up to 50% by weight consists of one or more metal oxides in atomic distribution of the group of elements consisting of Mo, Sn, Zn, V, Mn, Fe, Co, Ni, As, Pb, Bi, Ru, Re, Cr, W, Nb, Hf, La, Ce, Gd, Ga, In, Tl, Ag, Cu, Li, K, Na, Be, Mg, Ca, Sr and Ba.

4. The amorphous microporous mixed oxides according to claim 1, additionally containing up to 5% by weight of at least one of the elements Pt, Rh, Ir, Os, Ru, Re, Ag, Au, Cu, Ni, Pd, Co in highly dispersed form in a metallic or non-metallic state.

5. A process for the preparation of highly porous mixed oxides according to claim 1, wherein alkyloxy- or aryloxysilanes of the type R'Si(OR)$_3$ with non-hydrolyzable R' groups, wherein R'=methyl, ethyl, isopropyl, —$C_nH_{2n+1}$, phenyl, —$C_nH_{2n}Cl$, —$C_nH_{2n}NH_2$, —$C_nH_{2n}COOH$, —$C_nH_{2n}OH$, —$C_nH_{2n}CF_3$, —$CH_2CH=CH_2$, —$CH_2COCH_3$, —$CH_2NR_4^+$ or o-, m- or p-functionalized aryl groups, with or without a solvent are copolycondensated with soluble hydrolyzable derivatives of elements of the group consisting of Mo, Sn, Zn, V, Mn, Fe, Co, Ni, As, Pb, Bi, Ru, Re, Cr, W, Nb, Hf, La, Ce, Gd, Ga, In, Tl, Ag, Cu, Li, K, Na, Be, Mg, Ca, Sr, Ba, Pt, Rh, Ir, Os, Ru, Au, Pd, Ti, Si, Al, Zr at pH<7 without the application of pressure or supercritical conditions, and then dried.

6. The process according to claim 5 wherein soluble alkoxides, 1,3-dicarbonylates, carboxylates or salts are employed as said hydrolyzable derivatives.

* * * * *